US011116428B2

(12) United States Patent
Iuele et al.

(10) Patent No.: US 11,116,428 B2
(45) Date of Patent: Sep. 14, 2021

(54) BIOSENSOR FOR SENSING ANALYTES IN THE SWEAT, AND MANUFACTURING METHOD THEREOF

(71) Applicant: STMICROELECTRONICS S.R.L., Agrate Brianza (IT)

(72) Inventors: Helena Iuele, Potenza (IT); Vincenza Di Palma, Cimitile (IT)

(73) Assignee: STMICROELECTRONICS S.R.L., Agrate Brianza (IT)

( * ) Notice: Subject to any disclaimer, the term of this patent is extended or adjusted under 35 U.S.C. 154(b) by 708 days.

(21) Appl. No.: 15/163,822

(22) Filed: May 25, 2016

(65) Prior Publication Data
US 2017/0086715 A1 Mar. 30, 2017

(30) Foreign Application Priority Data
Sep. 30, 2015 (IT) .................. 102015000056972

(51) Int. Cl.
  *A61B 5/145* (2006.01)
  *G01N 33/543* (2006.01)
  (Continued)

(52) U.S. Cl.
  CPC ........ *A61B 5/14517* (2013.01); *A61B 5/1486* (2013.01); *A61B 5/14532* (2013.01);
  (Continued)

(58) Field of Classification Search
  None
  See application file for complete search history.

(56) References Cited

U.S. PATENT DOCUMENTS 5,735,273 A * 4/1998 Kurnik ................. A61B 5/1486
    600/345
6,120,676 A * 9/2000 Heller .................. A61B 5/1411
    205/775
(Continued)

FOREIGN PATENT DOCUMENTS

WO          9938003 A1    7/1999

OTHER PUBLICATIONS

Yan et al., "Immobilizing Enzymes Onto Electrode Arrays by Hydrogel Photolithography to Fabricate Multi-Analyte Electrochemical Biosensors," Applied Materials & Interfaces, vol. 2, No. 3, Feb. 16, 2010, pp. 748-755.

(Continued)

Primary Examiner — Kaylee R Wilson
Assistant Examiner — Jay B Shah
(74) Attorney, Agent, or Firm — Slater Matsil, LLP

(57) ABSTRACT

A biosensor is for sensing analytes in a fluid. The biosensor may include a first structural layer having a first hydrogel, a second structural layer having a second hydrogel, and a bioactive region extending between the first structural layer and the second structural layer and having a third hydrogel. The biosensor may include a first electrode coupled to the bioactive region, and a second electrode coupled to the first structural layer and being spaced apart from the bioactive region. The second structural layer may have a through opening adjacent the bioactive region, and the bioactive region may be configured to be in fluid communication with an environment external to the biosensor for receiving the fluid comprising the analytes.

20 Claims, 8 Drawing Sheets

(51) Int. Cl.
*C12Q 1/00* (2006.01)
*A61B 5/1486* (2006.01)

(52) U.S. Cl.
CPC .......... *A61B 5/14546* (2013.01); *C12Q 1/004* (2013.01); *G01N 33/5436* (2013.01); *A61B 2562/125* (2013.01)

(56) References Cited

U.S. PATENT DOCUMENTS

| | | |
|---|---|---|
| 6,485,703 B1 | 11/2002 | Cote et al. |
| 2007/0189928 A1* | 8/2007 | Sabol .................. A61B 5/1486 422/82.03 |
| 2010/0200538 A1 | 8/2010 | Petisce et al. |
| 2014/0017772 A1 | 1/2014 | Di Matteo et al. |

OTHER PUBLICATIONS

Makaram et al., "Trends in Nanomaterial-Based Non-Invasive Diabetes Sensing Technologies," Diagnostics 2014, 4, Apr. 21, 2014, pp. 27-46.

Gibas et al., "Review: Synthetic Polymer Hydrogels for Biomedical Applications," Chemistry & Chemical Technology, vol. 4, No. 4, Jan. 1, 2010, pp. 297-304.

* cited by examiner

BIOSENSOR FOR SENSING ANALYTES IN THE SWEAT, AND MANUFACTURING METHOD THEREOF

RELATED APPLICATION

This application is based upon prior filed copending Italian Application No. 102015000056972 filed Sep. 30, 2015, the entire subject matter of which is incorporated herein by reference in its entirety.

TECHNICAL FIELD

The present invention relates to a biosensor, and more particularly to a biosensor for sensing analytes in a fluid and related methods.

BACKGROUND

In medical diagnostics, wearable biosensors are helpful for supplying information regarding the current state of health of a patient. A biosensor is a device for sensing an analyte. A biosensor comprises a bio-recognition element (i.e. a sensitive biological element) and a sensing element that coverts the signal resulting from interaction of the analyte with the sensitive biological element into a signal that may easily be measured and quantified.

Analysis of sweat, in particular, is receiving particular attention for analysis of glucose and lactate in so far as, unlike analyses based upon blood samples, it does not require invasive procedures for acquisition of the sample to be analyzed. Electrolytes are the components of sweat that may be analyzed most easily. Metabolites, such as, for example, lactate and glucose, are more difficult to measure. However, there is interest in monitoring these metabolites on account of their fundamental diagnostic role. Lactate, for example, is an indicator of a deficiency of oxygen; an excessive increase of lactate is a symptom of ischaemia and is an indicator of some types of cancer. Monitoring of glucose, instead, is of fundamental importance in management of diabetes. There is a direct correlation between the concentrations of glucose and lactate in blood and those present in the sweat.

The current approaches used for monitoring metabolites through analysis of sweat evision using a typical technique, such as reverse iontophoresis. Devices based upon reverse iontophoresis are provided with electrical terminals (i.e. cathode and anode), arranged in contact with the skin of the patient, between which an electric current may flow. Supply between the cathode and the anode of the device of a low electric current, through the skin of the patient, causes an osmotic migration of sodium and chloride ions that transport the glucose and lactate molecules present in the sweat towards the cathode and the anode, respectively. Arranged on one of them is the enzyme specific for the analyte, so that from the enzyme-analyte interaction it is possible to measure the analyte concentration. However, devices based upon this technology may cause discomfort or irritation to the skin of sensitive patients on account of the presence of the electric current that flows through the skin itself.

SUMMARY

A biosensor is for sensing analytes in a fluid. The biosensor may include a first structural layer having a first hydrogel, a second structural layer having a second hydrogel, and a bioactive region extending between the first structural layer and the second structural layer and having a third hydrogel. The biosensor may include a first electrode coupled to the bioactive region, and a second electrode coupled to the first structural layer and being spaced apart from the bioactive region. The second structural layer may have a through opening adjacent the bioactive region, and the bioactive region may be configured to be in fluid communication with an environment external to the biosensor for receiving the fluid comprising the analytes.

DETAILED DESCRIPTION

Figure 1:
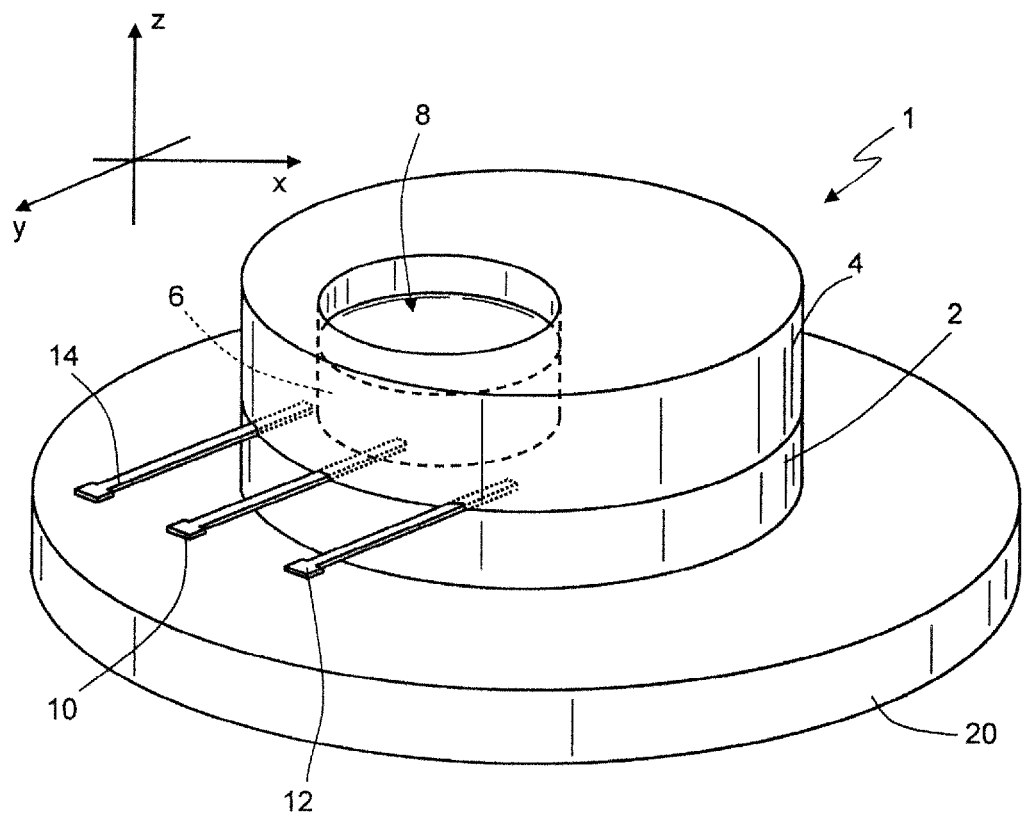
FIG. 1 is a schematic perspective view of a biosensor, according to an embodiment of the present disclosure.
Figure 2:
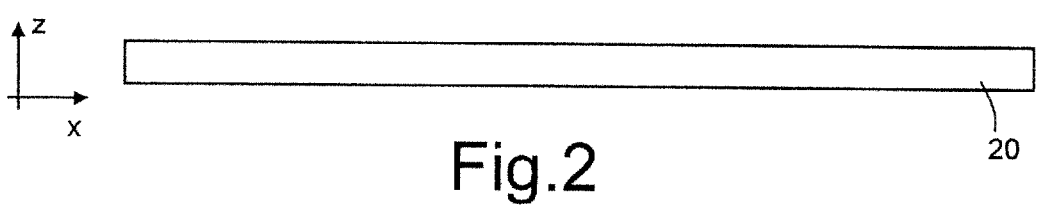
FIGS. 2-11 are schematic cross-section views of steps for making the biosensor of FIG. 1.
Figure 3:
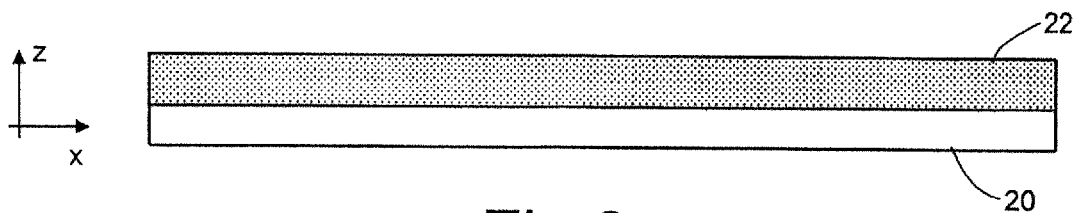
Figure 4:
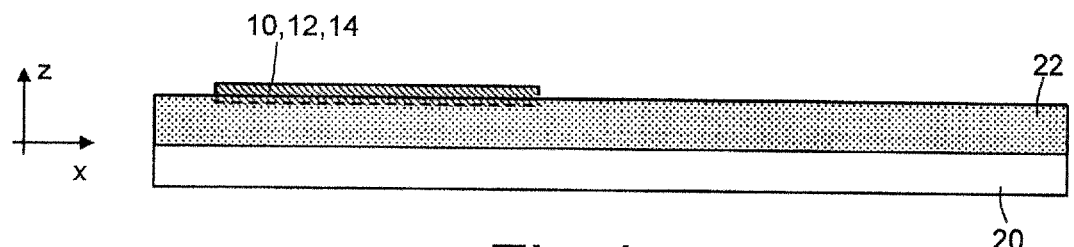
Figure 5:
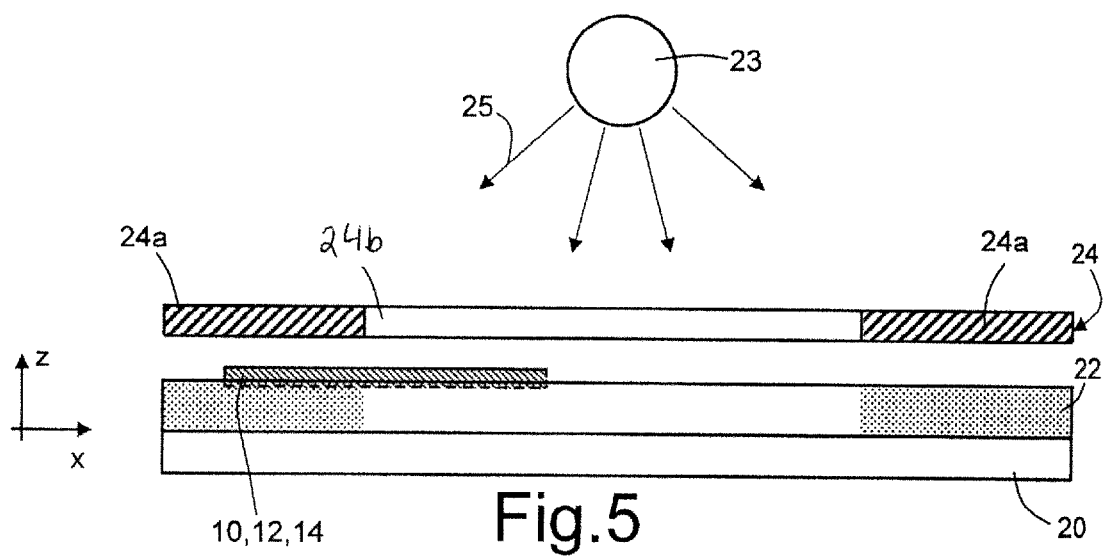

FIG. 1 includes, in a triaxial reference system X, Y, Z, a biosensor 1. The biosensor 1 comprises a first structural layer 2 of photosensitive hydrogel; a second structural layer 4, of photosensitive hydrogel, which extends over the first structural layer 2; and a sensing region 6, including a matrix of photosensitive hydrogel dispersed in which are bio-recognition elements, in particular enzymes such as GOx (glucose oxidase) and LOx (lactate oxidase). The second structural layer 4 has a through opening 8 in the sensing region 6 such that the sensing region 6 is, at least partially, exposed towards the outer environment through the through opening 8.

A working electrical terminal 10 is arranged in electrical contact with the sensing region 6. Whereas a counter-electrode electrical terminal 12 is arranged on the first layer 2 (or, in part, in the first layer 2), alongside the sensing region 6, and not in direct electrical contact with the sensing region 6. A reference electrical terminal 14 extends over the first layer 2 (or, in part, in the first layer 2), alongside the sensing region 6, and not in direct electrical contact with the sensing region 6. In particular, the sensing region 6 extends, in top plan view in the plane XY, between the counter-electrode electrical terminal 12 and the reference electrical terminal 14.

The working electrical terminal 10, the counter-electrode electrical terminal 12 and the reference electrical terminal 14 are made of conductive material, such as, for example, an inert metal chosen from gold, silver, platinum, conductive polymers, and carbon. The reference electrode 14 may likewise be made of silver chloride, AgCl. The biosensor 1 provides, in practice, an electrochemical cell with three electrodes.

Hydrogels, which are typical in the state of the art, are particularly attractive for manufacture of biochemical sensors since they are constituted by polymeric chains of hydrophilic molecules that form an excellent matrix for encapsulating functional enzymes, cells, and other biological material. In particular, the environmental conditions within the hydrogel are ideal for minimizing denaturation of the biological elements dispersed therein, favoring functionality thereof.

The photosensitive hydrogel used for forming the first structural layer 2, the second structural layer 4, and the sensing region 6 includes hydrophilic polymers that comprise polymeric chains cross-linked with one another with both covalent bonds and non-covalent bonds. Their monomers or pre-polymers are soluble in water, whereas the polymers are insoluble in water at physiological temperature, pH, and ionic force. The water content (% $H_2O$) is defined as % $H_2O$=100·(swollen-polymer weight/dry-polymer weight)/(swollen-polymer weight). The polymers may have a molecular weight in the range of 500-200000 dalton, and their properties including viscosity, softening point, and degradation temperature are optimized according to the specific application.

The first structural layer 2, the second structural layer 4, and the sensing region 6 may comprise: monomers, oligomers, or pre-polymers (the molecular weight of pre-polymers controls the mechanical properties and viscosity), or binders that regulate the mechanical properties of the mixture (adhesion, etc.); one or more solvents that further control the mechanical properties, such as for example the viscosity of the mixture; and photo-active compounds (PACs) or photo-inhibitors (PhIs). According to one embodiment of the present disclosure, the hydrogel of the first structural layer 2, of the second structural layer 4, and of the sensing region 6 functions like a negative photoresist used in photolithographic processes, so that controlled ultraviolet (UV) irradiation of a portion of the second structural layer 4 and of the sensing region 6 causes polymerization of just the irradiated regions, enabling removal of the non-irradiated regions by development in water. In this case, thus, the hydrogel contains monomers or oligomers or precursor pre-polymers, and by exposure to incident UV radiation, for example, undergoes a reaction of photo-polymerization and/or photo-cross-linking. Photo-cross-linking of the layers involved determines an increase of their molecular weight, which causes an advantageous reduction of the solubility of the layers in water.

Examples of hydrogels made up of simple monomers or mixtures of different monomers, which may be used according to the present disclosure, are:

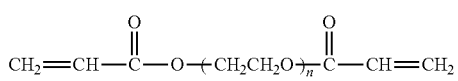

polyethylene glycol diacrylate (PEG-DA),

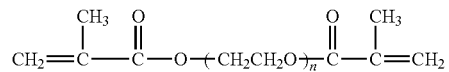

PEG dimethacrylate,

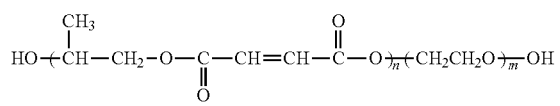

polypropylene fumarate-co-ethylene glycol,

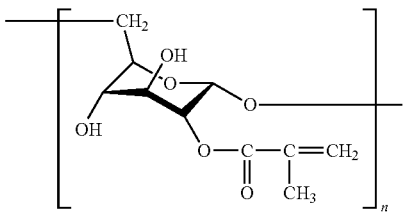

dextran modified with methacrylate,

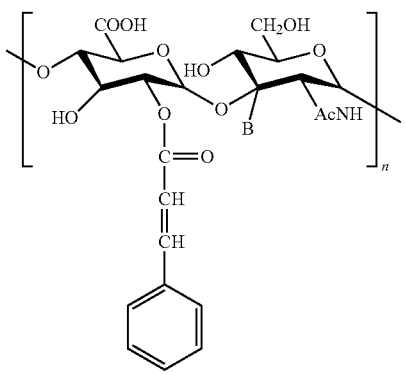

Commutated hyaluronic acid,

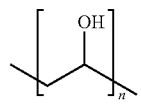

polyvinyl alcohol (PVA)

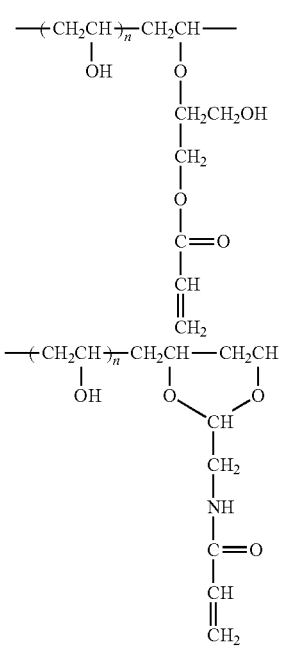

PVA modified with acrylate,

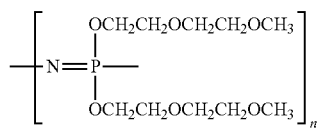

poly[bis(methoxyethoxyethoxy)phosphazene] (MEEP),

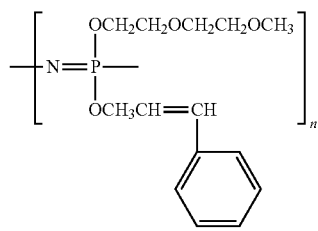

Polyphosphazene,

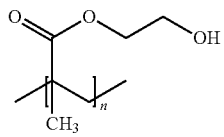

Polyhydroxyethylmethacrylate (PHEMA)

In the rest of the description, reference will be made to PEG-DA without this implying any loss of generality. FIGS. 2-11 show, in lateral view in the plane XZ, successive steps of manufacture the biosensor 1 of FIG. 1, according to one aspect of the present disclosure. A substrate 20 is first prepared (FIG. 2), for example of glass, or silicon, or plastic material (e.g., polyethylene terephthalate, polyethylene terephthalate (PET), polyethylene naphthalate, polyethylene naphthalate (PEN), polyether ether ketone, polyether ether ketone (PEEK)).

Then (FIG. 3), a first photo-definable hydrogel layer 22 is formed on the substrate 20, as described in what follows. A pre-polymeric mixture is prepared by adding a PEG-DA photo-initiator, in a percentage of 2-3% v/v. Any photo-initiator, with the capacity of absorbing UV radiation and undergoing photoreaction, producing reactive species, radicals that polymerize, and constituents of the pre-polymeric mixture is suited for the purpose. In particular, 2-hydroxy-2-methyl-1-phenylpropan-1-one, also commercially known as Darocur™ is used as photo-initiator. The pre-polymeric solution thus formed is deposited, using the spin-coating technique, on the substrate 20 (at 700-1000 rpm, for 8-15 s, in particular 800 rpm for 10 s).

The first photo-definable hydrogel layer 22 has a thickness comprised between 100 nm and 1000 nm, for example 200 nm. The deposition parameters may be adjusted according to the viscosity of the hydrogel-based solution used for obtaining a layer 22 having the desired thickness.

The next step (FIG. 4) is the arrangement of (commercially available) conductive filaments that form the working electrical terminal 10, the counter-electrode electrical terminal 12, and the reference electrical terminal 14. The aforesaid filaments have, for example, a diameter between 50 nm and 200 nm and are made of a material chosen from gold, silver, platinum, conductive polymers, and carbon.

The filaments are arranged on the layer 22 prior to the cross-linking step. The filaments penetrate only partially into the layer 22. In this way, they (and in particular the working electrical terminal 10) are electrically accessible from above.

Then (FIG. 5), a cross-linking step is carried out, using a UV lamp 23 that generates UV radiation 25, on selective portions of the first photo-definable hydrogel layer 22. In particular, in order to obtain selective polymerization of the first photo-definable hydrogel layer 22, a mask 24 is used provided with opaque regions 24a, which are designed to block the incident UV radiation 25, and transparent regions 24b, which are transparent to the incident UV radiation 25. In this way, only the portions of the first photo-definable hydrogel layer 22 that extend in the transparent regions 24b undergo a process of cross-linking since the hydrogel behaves like a negative photoresist.

Figure 6:
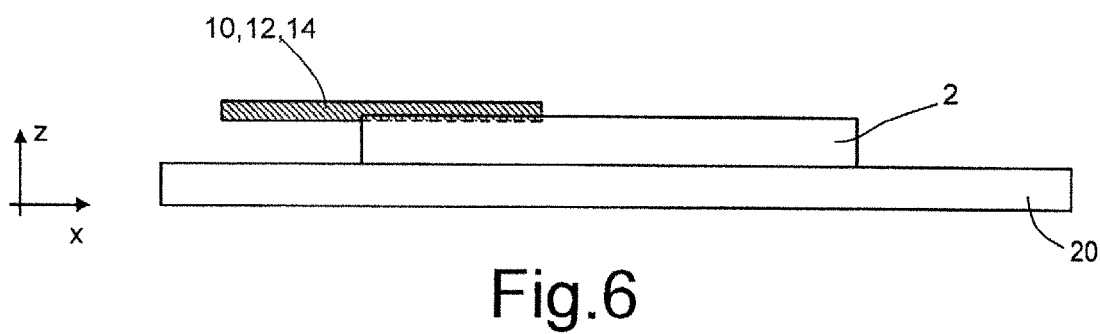
Figure 7:
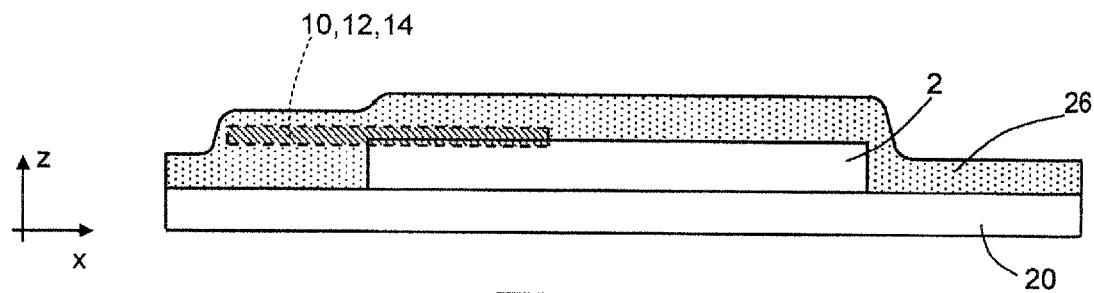
Figure 8:
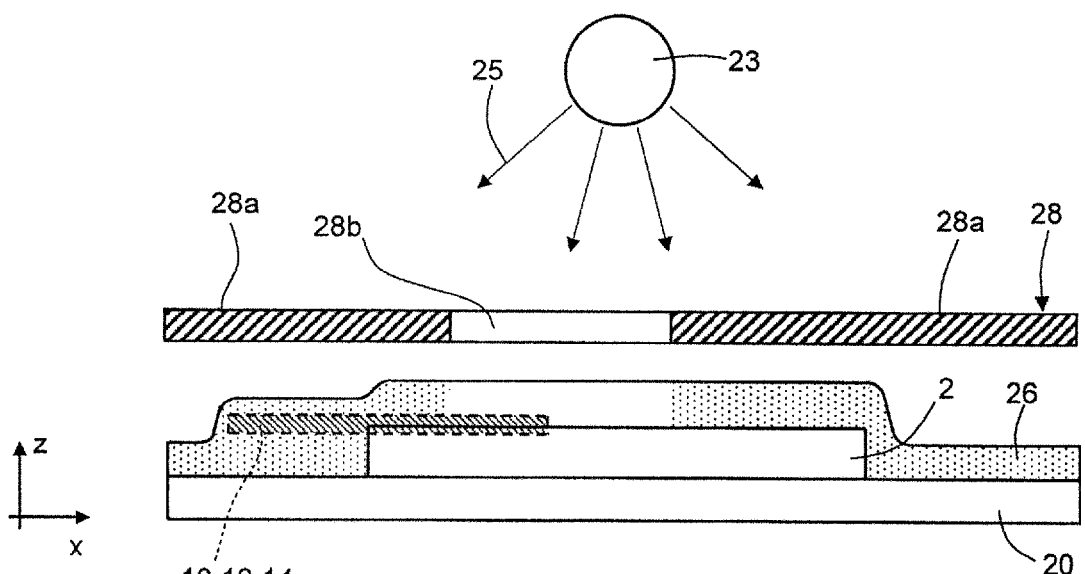
Figure 9:
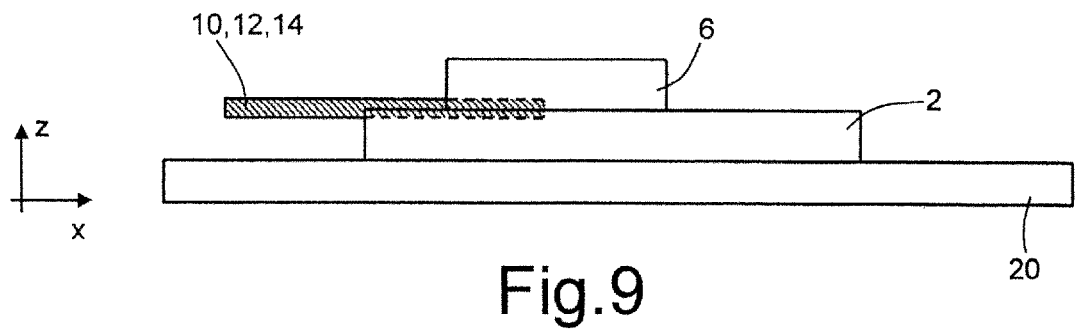
Figure 10:
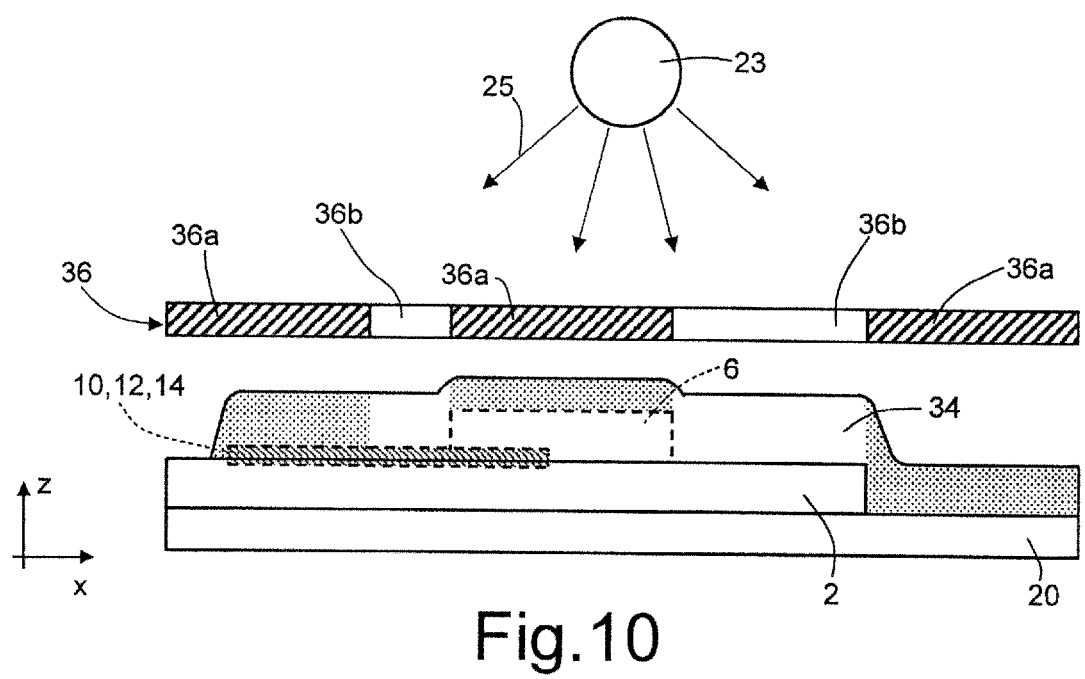

According to one aspect of the present disclosure, the filaments, which form the working electrical terminal 10, the counter-electrode electrical terminal 12, and the reference electrical terminal 14, extend partially inside the regions of the first photo-definable hydrogel layer 22 that are polymerized and partially outside so that, as illustrated in FIG. 6, after the polymerization step, the filaments will be electrically accessible from outside the first structural layer 2 formed.

The polymerization step is carried out using the following exposure parameters: wavelength of UV radiation chosen according to the photo-initiator used, for example (in the case of use of Darocur™), 365 nm; exposure power comprised in the range between 12 mW/cm$^2$ and 20 mW/cm$^2$, in particular 18 mW/cm$^2$; exposure time comprised between 5 s and 20 s, in particular 7 s. A subsequent step of bathing in deionized water enables removal in a few minutes of the portions of the first non-polymerized photo-definable hydrogel layer 22, to form the first structural layer 2, as illustrated in FIG. 6.

Then (FIG. 7), a second photo-definable hydrogel layer 26 (provided with bio-recognition elements, for example enzymes) is formed on the substrate 20 and the first structural layer 2. The second photo-definable hydrogel layer 26 forms the sensing region 6 in subsequent manufacturing steps.

In detail, the second photo-definable hydrogel layer 26 is formed starting from a pre-polymeric solution of hydrogel (e.g., PEG-DA), a photo-initiator (e.g., Darocur™) at 3% v/v, and an reduction-oxidation (redox) mediator at 1% v/v. The redox mediator is a molecule able to mediate a reduction-oxidation reaction or, in other words, able to facilitate the flow of electrons, generated by the reduction-oxidation reaction, through the hydrogel matrix. The redox mediator is, for example, a derivative of ferrocene, such as vinylferrocene.

An enzymatic solution is prepared by dissolving appropriate enzymes in a phosphate buffer (PBS), with pH ranging between 6 and 6.5, and glutaraldehyde as agent for improving retention of the enzyme in the matrix. The enzymes are chosen, according to one embodiment, from between glucose oxidase (GOx) and lactate oxidase (LOx). The concentration of the enzymes in PBS is, for example, 20 mg/mL.

The pre-polymeric solution and the enzymatic solution thus prepared are mixed together for a time comprised between 4 h and 5 h at a temperature comprised between 4° C. and 5° C. (e.g., 4° C.). The ratio between the pre-polymeric solution and the enzymatic solution is 10:1 v/v but may be varied according to the need. The mixture thus obtained (known as "sensing matrix") forms the second photo-definible hydrogel layer 26, which is deposited on the substrate 20 and on the first structural layer 2 using the spin-coating technique, in a way similar to what has already been described with reference to the first photo-definible hydrogel layer 22. The second photo-definible hydrogel layer 26 has a thickness comprised between 100 nm and 1000 nm, for example 200 nm. Also in this case, the deposition parameters may be adjusted according to the viscosity of the solution used for the second photo-definible hydrogel layer 26 for obtaining a layer 26 (and thus the sensing region 6) having the desired thickness.

Then (FIG. 8), a step of exposure to UV radiation is carried out to favor cross-linking of selective portions of the second photo-definible hydrogel layer 26, using an appropriate mask 28. Exposure is obtained, for example, using the same UV lamp 23 used previously, which generates UV radiation 25. In order to obtain selective polymerization of the second photo-definible hydrogel layer 26, the mask 28 is used provided with opaque regions 28a, which are designed to block the incident UV radiation 25, and transparent regions 28b, which are transparent to the incident UV radiation 25. In this way, only the portions of the second photo-definible hydrogel layer 26 that extend in the transparent regions 28b are subjected to a cross-linking process.

According to one aspect of the present disclosure, the metal filament that forms the working electrical terminal 10 extends partially inside the regions of the second photo-definible hydrogel layer 26, which is polymerized, and partially outside so that, after the polymerization step, the filament will be electrically accessible from outside the sensing region 6 thus formed. The polymerization step is carried out using the following exposure parameters: wavelength of the UV radiation chosen according to the photo-initiator used, for example, (in the case of use of Darocur™) 365 nm; exposure power comprised in the range between 12 mW/cm$^2$ and 20 mW/cm$^2$, in particular 18 mW/Cm$^2$; exposure time comprised between 5 s and 20 s, in particular 7 s.

Next (FIG. 9), a step of bathing in deionized water is carried out, which enables removal in a few minutes of the portions of the second photo-definible hydrogel layer 26 that has not been polymerized, to form the sensing region 6 in an area corresponding to the working electrode 10 and in electrical contact therewith. Next (FIG. 10), the second structural layer 4 is formed. For this purpose, a third photo-definible hydrogel layer 34 is formed on the substrate 20, on the first structural layer 2, and on the sensing region 6.

For this purpose, a pre-polymeric mixture is prepared by adding to polyethylene glycol diacrylate (in what follows, PEG-DA) a photo-initiator, in a percentage of 2-3% v/v, as described with reference to the first photo-definible hydrogel layer 22. In particular, 2-hydroxy-2-methyl-1-phenylpropan-1-one, also known commercially as Darocur™, is used as photo-initiator. The pre-polymeric solution thus formed is deposited, using the spin-coating technique, on the substrate 20, on the first structural layer 2, and on the sensing region 6. Spin-coating is carried out between 700 rpm and 1000 rpm, for 8-15 s, in particular 800 rpm for 10 s.

The third photo-definible hydrogel layer 34 thus formed has a thickness comprised between 100 nm and 1000 nm, for example 200 nm. The deposition parameters may be adjusted according to the viscosity of the hydrogel-based solution used for obtaining a layer 34 having the desired thickness. Once again with reference to FIG. 10, a step of exposure to UV radiation is carried out to favor cross-linking of selective portions of the third photo-definible hydrogel layer 34, using an appropriate mask 36. Exposure is obtained, for example, using the same UV lamp 23 used previously, which generates UV radiation 25. In order to obtain selective polymerization of the third photo-definible hydrogel layer 34, the mask 36 is provided with opaque regions 36a, designed to block the incident UV radiation 25, and transparent regions 36b, transparent to the incident UV radiation 25. In this way, only the portions of the third photo-definible hydrogel layer 34 that extend in the transparent regions 36b are subjected to a cross-linking process.

Figure 11:
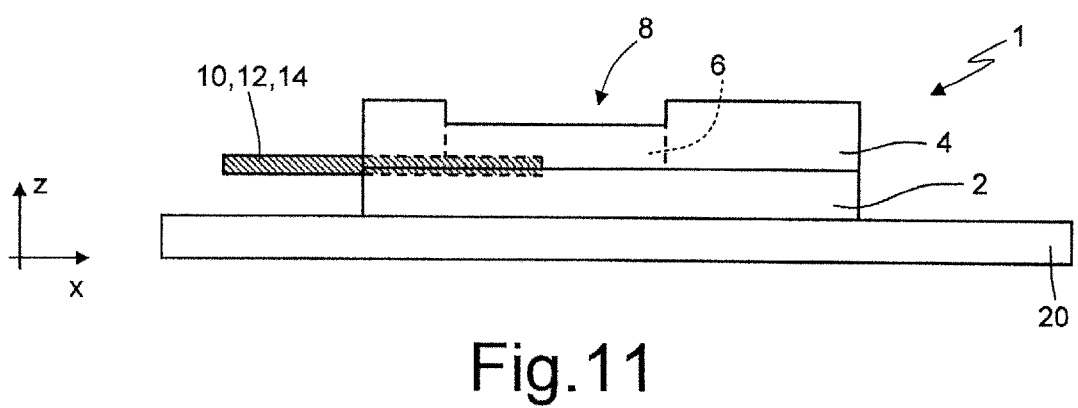

The step of polymerization of the third photo-definible hydrogel layer 34 is carried out using the following exposure parameters: wavelength of UV radiation chosen according to the photo-initiator used, for example, (in the case of use of Darocur™) 365 nm; exposure power comprised in the range between 12 mW/cm$^2$ and 20 mW/cm$^2$, in particular 18 mW/cm$^2$; exposure time comprised between 5 s and 20 s, in particular 7 s. A subsequent step of development in deionized water enables removal of the portions of the third non-polymerized photo-definible hydrogel layer 34, to form the second structural layer 4, as illustrated in FIG. 11.

According to the present disclosure, the mask 36 is provided with an opaque region that covers, in use (i.e., when the mask 36 is arranged aligned to the third photo-definible hydrogel layer 34), the portion of the third photo-definible hydrogel layer 34 that extends over the sensing region 6. In this way, the portion of the third photo-definible hydrogel layer 34 on the sensing region 6 does not undergo the cross-linking process and is removed during the step of development in deionized water. The through opening 8 is thus formed, through which the sensing region 6 is exposed, at least in part. The biosensor 1 of FIG. 1 is thus formed. Finally, by a peeling step, the substrate 20 is removed to obtain the biosensor 1 of FIG. 1. The step of peeling of the substrate 20 is optional.

Figure 12:
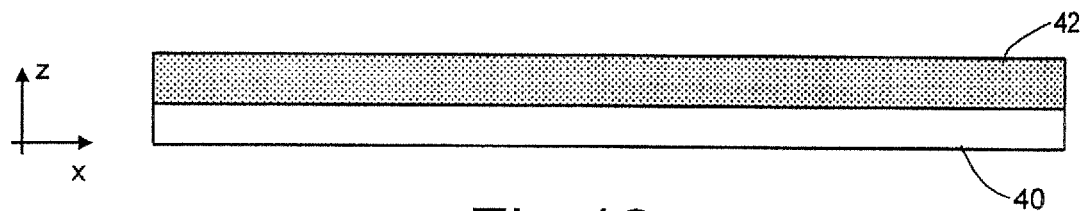
FIGS. 12-18 are schematic cross-section views of steps for making another embodiment of the biosensor.
Figure 13:
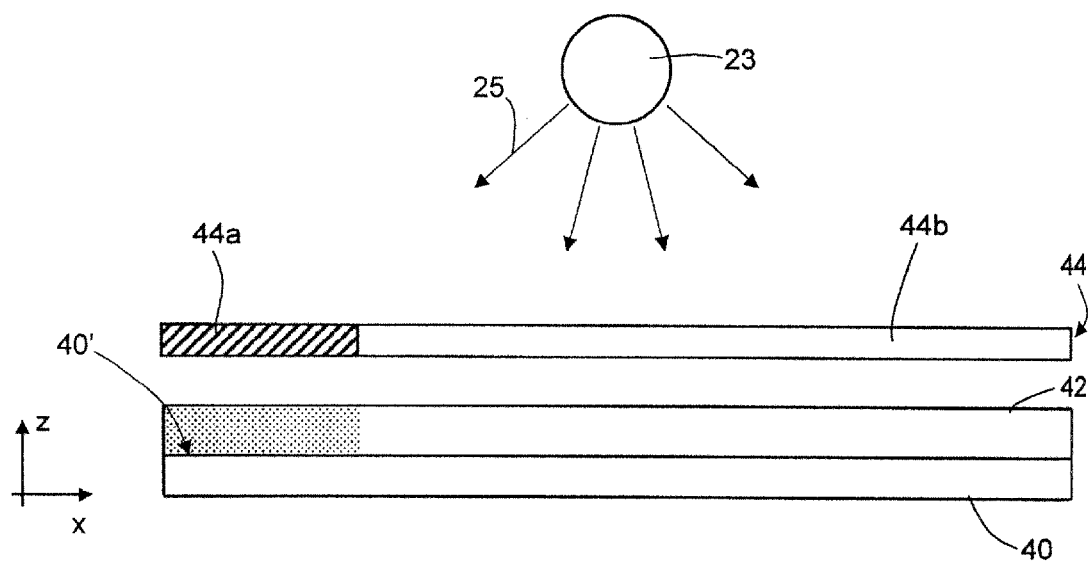
Figure 14:
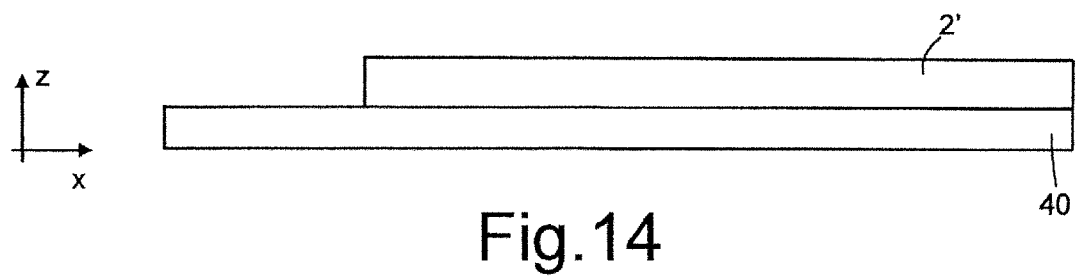

FIGS. 12-19 show steps for manufacturing a biosensor 1' according to a further embodiment. With reference to FIG. 12, a substrate 40 is first prepared, for example, glass, or silicon, or plastic material (e.g., PET, PEN, PEEK). Then, a first photo-definible hydrogel layer 42 is formed on the substrate 40 in a way similar to what has been described with reference to the layer 22 of FIG. 3, and not described any further herein.

Next (FIG. 13), a cross-linking step is carried out, using a UV lamp 23 which generates UV radiation 25, on selective portions of the first photo-definible hydrogel layer 42. In particular, in order to obtain selective polymerization of the first photo-definible hydrogel layer 42, a mask 44 is used provided with opaque regions 44a, which are designed to block the incident UV radiation 25, and transparent regions 44b, which are transparent to the incident UV radiation 25. In this way, only the portions of the first photo-definible hydrogel layer 42 that extend in the transparent regions 44b, undergo a cross-linking process.

In particular, the first photo-definible hydrogel layer 42 is not irradiated in a region thereof that extends over a portion 40' of the substrate 40 that, in subsequent manufacturing steps, will house the working electrical terminal 10', the counter-electrode electrical terminal 12', and the reference electrical terminal 14'. The portion 40' of the substrate 40 may be chosen freely according to the geometrical shape that it is desired to bestow on the first structural layer 2 (after the polymerization step); for example, the portion 40' of the substrate 40 extends along the periphery of the substrate 40.

Figure 15A:
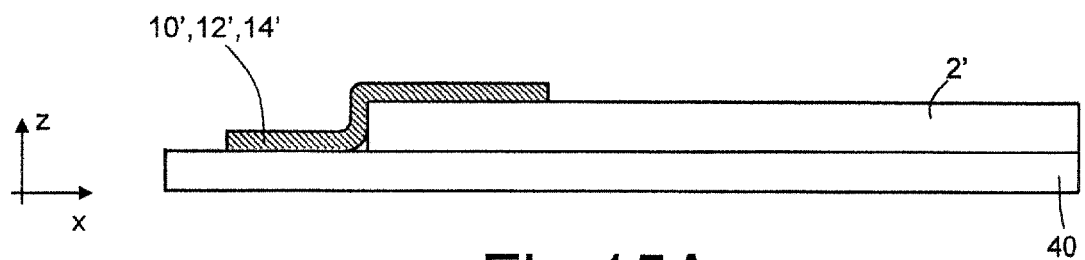

Next (FIG. 14), a bath in deionized water is carried out, which enables removal in a few minutes of the portions of the first non-polymerized photo-definible hydrogel layer 42 to form a first structural layer 2'. This is followed (FIG. 15A)

by a step of deposition, by sputtering, of metal material, such as for example gold deposition by sputtering is assisted by a mask (not illustrated) designed to enable deposition of the metal material in specific regions of the substrate 40 and of the first structural layer 2'. Metal strips are thus formed that extend from the surface of the first structural layer 2' towards the portion 40' of the substrate 40.

Figure 15B:
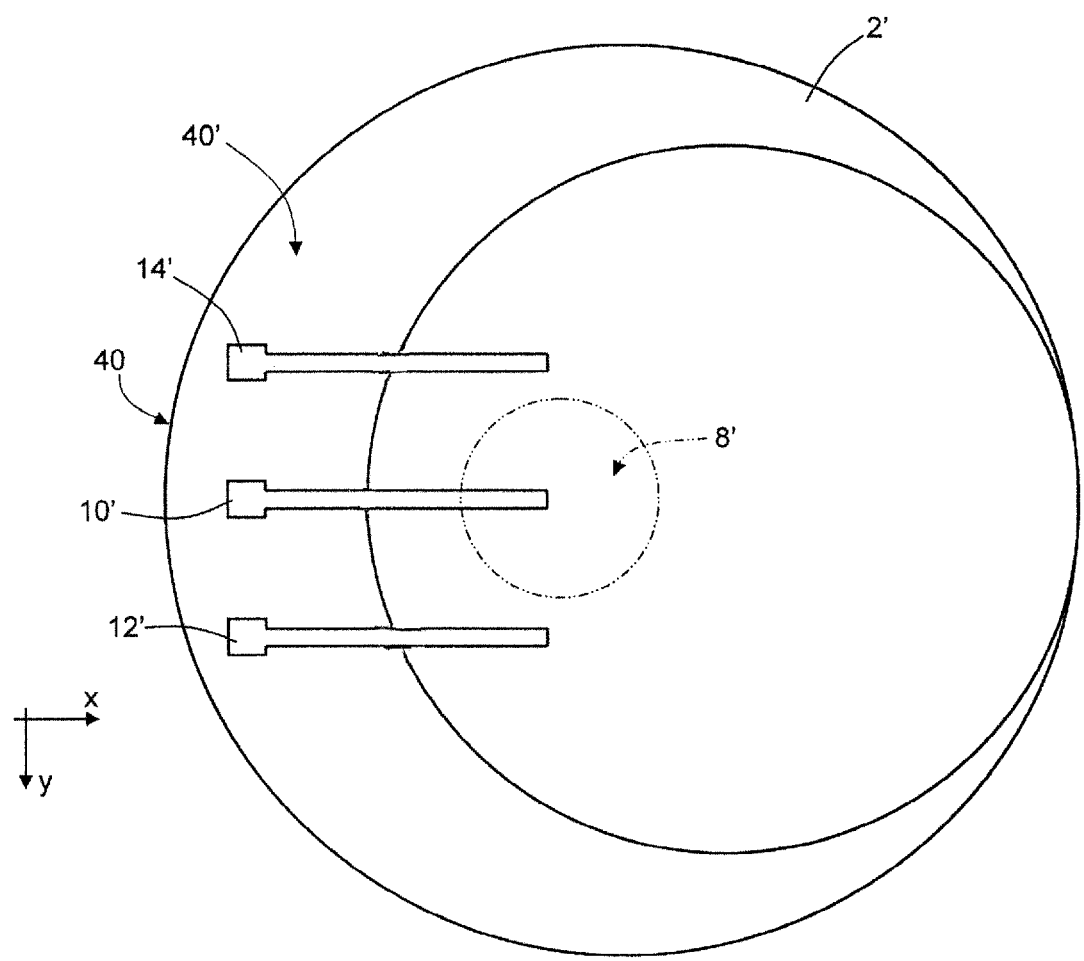
Figure 16:
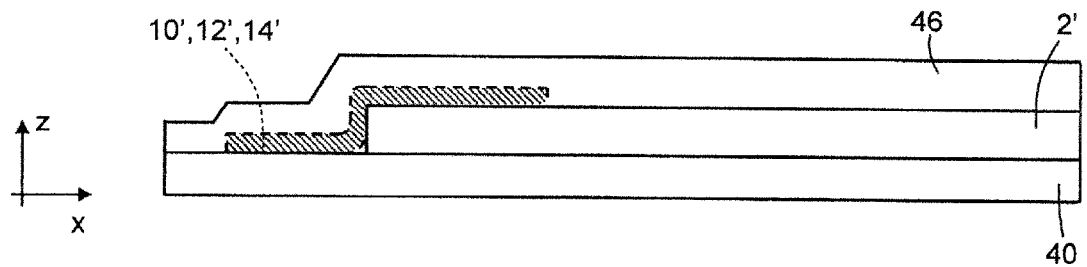

FIG. 15B shows, in top plan view in the plane XY, the substrate 40 provided with the first structural layer 2' and with the working electrical terminal 10', the counter-electrode electrical terminal 12', and the reference electrical terminal 14' thus formed. They may be made also of metals such as silver, platinum, or of conductive polymers, or carbon. Then (FIG. 16), a sensing region 6' is obtained, similar to the sensing region 6 of the biosensor 1.

For this purpose, a second photo-definible hydrogel layer 46 is formed (provided with bio-recognition elements, e.g. enzymes) on the substrate 40, the first structural layer 2', and the working electrical terminal 10', of the counter-electrode electrical terminal 12', and the reference electrical terminal 14'. The second photo-definible hydrogel layer 46 forms, in subsequent manufacturing steps, the sensing region 6'.

The second photo-definible hydrogel layer 46 is formed as described previously with reference to the second photo-definible hydrogel layer 26, starting from a pre-polymeric solution of hydrogel (e.g., PEG-DA), a photo-initiator (e.g., 2-hydroxy-2-methyl-1-phenylpropan-1-one) at 3% v/v, and a redox mediator (e.g., a derivative of ferrocene, such as vinylferrocene) at 1% v/v. An enzymatic solution is prepared by dissolving appropriate enzymes in a PBS phosphate buffer with pH levels ranging between 6 and 6.5 and glutaraldehyde as agent for improving retention of the enzyme in the matrix. The enzymes are chosen, according to one embodiment, between glucose oxidase (GOx) and lactate oxidase (LOx). The concentration of the enzymes in PBS is, for example, 20 mg/mL.

The pre-polymeric solution and the enzymatic solution thus prepared are mixed together for a time comprised between 4 h and 5 h at a temperature comprised between 4° C. and 5° C. (e.g., 4° C.). The ratio between the pre-polymeric solution and the enzymatic solution is 10:1 v/v, but may be varied according to the need. The mixture thus obtained (known as "sensing matrix") is deposited using the spin-coating technique and forms the second photo-definible hydrogel layer 46, in a way similar to what has already been described with reference to the second photo-definible hydrogel layer 26. The second photo-definible hydrogel layer 46 has a thickness comprised between 100 nm and 1000 nm, for example 200 nm. Also in this case, the deposition parameters may be adjusted according to the viscosity of the solution used for the second photo-definible hydrogel layer 46 for obtaining a layer 46 (and thus the sensing region 6') having the desired thickness.

Figure 17:
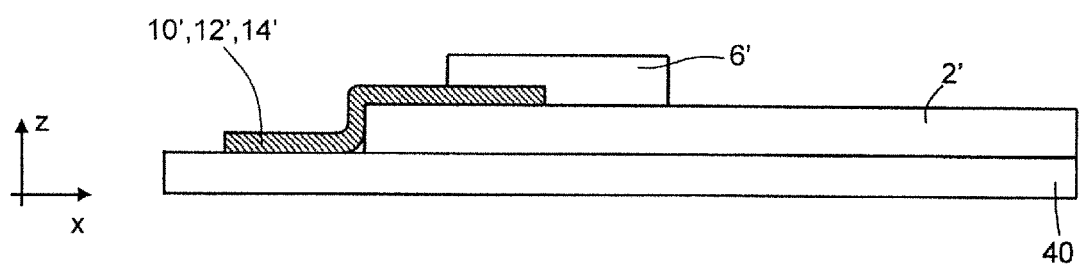
Figure 18:
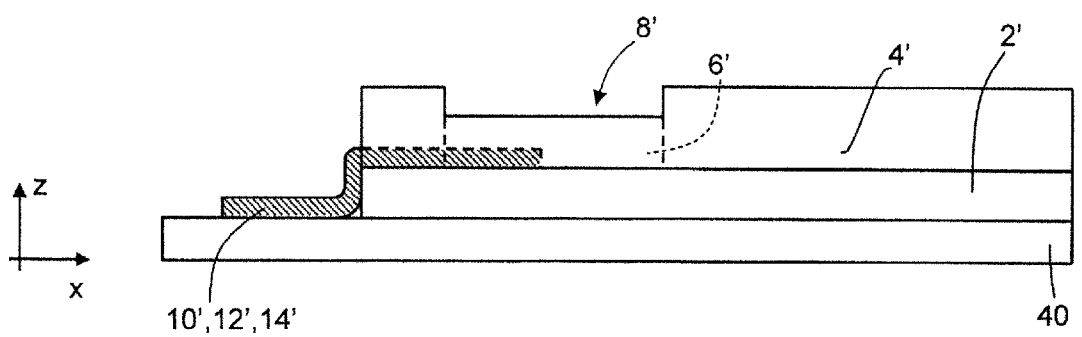

Next (FIG. 17, a step of exposure to UV radiation is carried out to favor cross-linking of selective portions of the second photo-definible hydrogel layer 46, using an appropriate mask (not illustrated). Exposure is obtained, for example, used the same UV lamp 23 previously used, which generates UV radiation 25. In order to obtain selective polymerization of the second photo-definible hydrogel layer 46, a mask is used provided with opaque regions, designed to block the incident UV radiation 25, and regions transparent to the incident UV radiation 25. In this way, only the portions of the second photo-definible hydrogel layer 46 aligned, along Z, to the transparent regions are subjected to a cross-linking process since the hydrogel behaves like a negative photoresist.

The polymerization step is carried out using the exposure parameters already previously indicated for polymerization of the second photo-definible hydrogel layer 26. A subsequent step of bathing in deionized water enables removal in a few minutes of the portions of the second photo-definible hydrogel layer 46 that has not been polymerized, to form the sensing region 6', as illustrated in FIG. 17.

After the step of removal of the hydrogel that has not been polymerized, only the metal path that forms the working electrical terminal 10' extends in direct contact with the sensing region 6'. The metal paths that form the counter-electrode electrical terminal 12' and reference electrical terminal 14' are not in direct contact with the sensing region 6', but extend alongside it.

Next (FIG. 18), a second structural layer 4' is formed, similar to the second structural layer 4 of the biosensor 1. The steps for producing the second structural layer 4' are similar to those described previously for the second structural layer 4 (see the description of FIGS. 10 and 11) and are not referred to any further herein. In particular, the process for producing the second structural layer 4' evisions formation of a through opening 8' in the sensing region 6'. The sensing region 6' is exposed, at least in part, through the through opening 8'.

Figure 19:
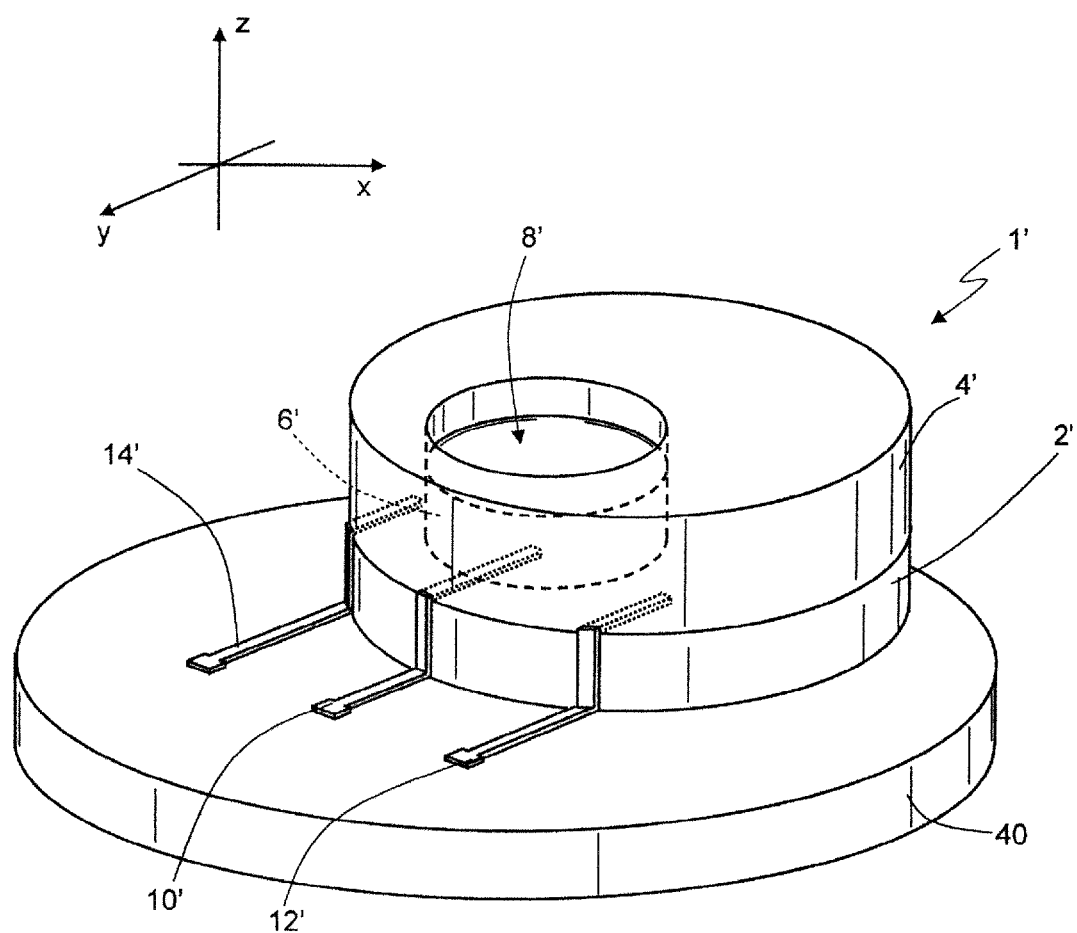
FIG. 19 is a schematic perspective view of yet another embodiment of the biosensor.

FIG. 19 shows, in perspective view, the biosensor 1' produced according to the steps of FIGS. 12-18. As may be noted from FIG. 19, in this embodiment the substrate 40 is not removed, in so far as it functions as support for the working electrical terminal 10', the counter-electrode electrical terminal 12', and the reference electrical terminal 14'. To favor adherence of the substrate 40 to the first structural layer 2', it is possible to insert an adhesive layer, for example an organosilane-based adhesive layer, between the substrate 40 and the first structural layer 2', prior to the step of deposition of the first hydrogel layer 42 of FIG. 12.

Functionalization of the substrate 40 with silane molecules is obtained according to a procedure, for example described in U.S. Pat. No. 9,244,067 to Di Matteo et al. In particular, the substrate is treated by an oxygen-plasma treatment (a common plasma-etching system is used for this purpose). A silane solution (2% v/v) is likewise prepared with 3-(trimethoxysilyl)propyl methacrylate in isopropyl alcohol, correcting the pH with acetic acid, to bring it to a value of 4.5-5. The solution then undergoes gentle stirring, and then it is necessary to wait a few minutes (i.e., at least 30 minutes) before using it. This enables hydrolysis of the siloxane groups.

The substrate 40 is then dipped in the silane solution, washed in isopropyl alcohol and then heated to 120° C. for 60 minutes. The substrate 40 is thus functionalized with silane molecules that expose methacrylic groups, to which the hydrogel 42 will subsequently bind during its polymerization, to form the state 2'. The silanes are chosen according to the type of hydrogel that is deposited on the substrate. In the case of PEG-DA-based hydrogel, the silanes may be chosen in the family of acrylate or methacrylate silanes, cyclic azosilanes, silanes with amine terminations, dipodal silanes, and carboxylate silanes.

The biosensor 1, 1' may be used by laying it directly on the skin of the patient to be monitored, so that the sensing region 6, 6' faces the skin through the through opening 8, 8'. The through opening 8, 8' formed through the second structural hydrogel layer 4, 4' provides, in use, a closed chamber that does not prevent natural transpiration of the skin, but considerably limits exchange of air with the external environment, causing a rapid increase of the local temperature of the skin up to values of approximately 35-40°

C. The vapor that is generated within the through opening 8, 8' saturates the environment and favors formation of sweat, which, coming into contact with the sensing region 6, 6', enables the biological analysis to be carried out. From the sweat produced glucose or lactate may in fact be monitored, thanks to the enzymes GOx or LOx present in the sensing matrix. Monitoring the current present between the working electrical terminal 10, 10' and the counter-electrode electrical terminal 12, 12' enables information to be obtained, in typical manner, on the analyte concentration monitored.

The present applicant has found that the hydrogel matrix used according to the present disclosure to create the sensing region 6, 6' provides a linear response in the range of concentrations of 10 µM to 4 mM for glucose, and 1 µM to 4 mM for lactate, i.e., in ranges compatible with the concentrations typically present in human sweat. In use, the biosensor 1 functions as amperometric sensor. As is known, an amperometric sensor is based upon the measurement of the current between the working electrical terminal 10 and the counter-electrode electrical terminal 12, a current that is induced by the redox reaction between the analyte and the enzyme that is obtained on the working electrical terminal 10. The current is proportional to the concentration of the analyte to be monitored. For this purpose, a constant potential (determined by the redox potential of the mediator, previously evaluated via cyclic voltammetric measurements) is applied to the electrochemical cell, and the response of the current is monitored. This potential enables operation in optimal conditions for monitoring of the current. In particular, the working electrode 10 is fixed at a potential, for example of 0.25 V, with respect to the reference electrical terminal 14. The value of 0.25 V is the peak anode potential, measured by the present applicant, of the mediator in vinylferrocene immobilized in the hydrogel matrix. The counter-electrode terminal is an auxiliary electrode and functions as drain of the current generated during the redox reaction on the working electrical terminal 10 (the counter-electrode 12 "collects" the electrons generated by the enzyme-analyte reaction).

The three-electrode configuration may provide the presence of a stable potential between the working electrical terminal 10 and the reference electrical terminal 14. However, other configurations, in particular a configuration with two electrodes (in which the reference electrode coincides with the counter-electrode) may likewise be used according to a further aspect of the present disclosure.

A potentiostat (not illustrated in the figures) may be operatively coupled to the working electrical terminal 10, to the counter-electrode electrical terminal 12, and to the reference electrical terminal 14, and is configured to control the voltage through the working terminal/counter-electrode terminal pair and to adjust it to maintain the difference of potential imposed between the working terminal 10 and the reference terminal 14. The reference electrical terminal measures and controls the potential of the working electrical terminal 10, while the counter-electrode electrical terminal 12 allows passage of all the other for balancing the current that is still observed on the working electrical terminal 10. With this arrangement, the current generated by the redox reaction is made to pass between the working terminal 10 and the counter-electrode terminal 12. This current, which may be measured, indicates a concentration of electroactive species present in the analyte.

The biosensor 1' functions in a way similar to the biosensor 1, according to what has been described above. The advantages that may be obtained with the invention described are evident from the foregoing description. In particular, the first structural layer 2 and the second structural layer 4 operate as a capsule that supports, protects, and contains the sensing region 6 and, at the same time, function as insulating layer between the electrodes. Thus, further supporting and containment layers are not necessary, rendering the biosensor 1 simple and inexpensive to produce.

The manufacturing process evisions use of devices and technologies widely employed in the field of microfabrication of micro-electromechanical devices, and in particular the shape of the layers 2, 2', 4, 4' is defined through simple photolithographic steps. The biosensor 1, 1' may thus be integrated within more complex electronic devices or MEMS, exploiting the same manufacturing technology.

Use of the hydrogel enables a biosensor to be obtained that does not cause discomfort during use (being of flexible material) and that has the appearance, for example, of a small plaster. It is thus simple to use, self-contained, and aesthetically discreet. The biosensor in question further works at low potentials. It may further be integrated in a discreet way in medical devices or in other wearable devices, such as a bracelet. Since the analysis is conducted on the basis of the patient's sweat, use of the biosensor 1, 1' does not cause any pain.

Finally, it is clear that numerous modifications and variations may be made to what has been described and illustrated herein, all of which fall within the scope of the inventive idea, as defined in the annexed claims. For example, the electrical terminals 10, 10', 12, 12', 14, 14' may be obtained using other technologies, for example by ink-jet deposition. Furthermore, the bio-recognition elements trapped in the bioactive region 6 may be different from the enzymes GOx and Lox; for example, they may be chosen from enzymes of another type, or else from: antibodies, nucleic acids, and cell receptors.

That which is claimed is:

1. A biosensor for sensing analytes in a fluid, the biosensor comprising:
   a first structural layer on a substrate comprising a first photodefinible hydrogel;
   a second structural layer comprising a second photodefinible hydrogel;
   a bioactive region extending between said first structural layer and said second structural layer and comprising a third photodefinible hydrogel, a plurality of bio-recognition elements, and a reduction-oxidation mediator;
   a working electrode in contact with said bioactive region; and
   a counter-electrode in contact with said first structural layer and being spaced apart from said working electrode and said bioactive region, wherein a bottom surface of the counter-electrode is coplanar with a bottom surface of the working electrode in a first electrode portion over a surface of the substrate and in a second electrode portion over a surface of the first structural layer, and wherein the bottom surface of the counter-electrode and the bottom surface of the working electrode are immediately adjacent to a sidewall of the first structural layer in a third electrode portion between the first electrode portion and the second electrode portion;
   said second structural layer having a through opening adjacent said bioactive region; and
   said bioactive region configured to be in direct fluid connection with an environment external to the biosensor for receiving the fluid comprising the analytes to react with said plurality of bio-recognition elements and with the reduction-oxidation mediator.

2. The biosensor according to claim 1 wherein said bioactive region is in direct contact with said first structural layer and with said second structural layer.

3. The biosensor according to claim 1 wherein said first structural layer abuts a bottom surface of said bioactive region; and wherein said second structural layer laterally surrounds said bioactive region.

4. The biosensor according to claim 1 wherein said plurality of bio-recognition elements comprises enzymes.

5. The biosensor according to claim 4 wherein said enzymes comprise at least one of glucose oxidase and lactate oxidase.

6. The biosensor according to claim 1 wherein said bioactive region, said first structural layer, and said second structural layer each comprises at least one of a monomer, an oligomer, and a pre-polymer.

7. The biosensor according to claim 6 wherein said at least one of the oligomer and the pre-polymer is chosen from a group comprising:
   polyethylene glycol diacrylate (PEG-DA),
   PEG dimethacrylate,
   polypropylene fumarate-co-ethylene glycol,
   dextran modified with methacrylate,
   poly[bis(methoxyethoxyethoxy)phosphazene] (MEEP),
   commutated hyaluronic acid,
   polyvinyl alcohol (PVA) modified with acrylate,
   PVA,
   polyphosphazene,
   polyhydroxyethylmethacrylate (PHEMA).

8. The biosensor according to claim 1 further comprising a reference electrode in direct contact with said first structural layer and spaced apart from said bioactive region.

9. The biosensor according to claim 8 further comprising a potentiostat coupled to said working electrode, said counter-electrode, and said reference electrode and configured to keep said working electrode at a constant potential with respect to said reference electrode so that an electric current circulates between said working electrode and said counter-electrode; and wherein the electric current indicates a concentration of electroactive species present in the analytes.

10. The biosensor according to claim 8, wherein the working electrode, the counter-electrode, and the reference electrode comprise the same material and comprise the same shape in a plan view, and wherein an end of the working electrode is centrally located within the through opening in a plan view.

11. A biosensor for sensing analytes in a fluid, the biosensor comprising:
   a first structural layer on a substrate comprising a first hydrogel;
   a second structural layer comprising a second hydrogel;
   a bioactive region extending between said first structural layer and said second structural layer and comprising a third hydrogel;
   a first electrode coupled to said bioactive region; and
   a second electrode coupled to said first structural layer and being spaced apart from said first electrode and said bioactive region, wherein a bottom surface of the second electrode is coplanar with a bottom surface of the first electrode in a first electrode portion over a surface of the substrate and in a second electrode portion over a surface of the first structural layer, and wherein the bottom surface of the first electrode and the bottom surface of the second electrode are immediately adjacent to a sidewall of the first structural layer in a third electrode portion between the first electrode portion and the second electrode portion;
   said second structural layer having a through opening adjacent said bioactive region; and
   said bioactive region configured to be in fluid communication with an environment external to the biosensor for receiving the fluid comprising the analytes.

12. The biosensor according to claim 11 wherein said bioactive region is coupled to said first structural layer and with said second structural layer.

13. The biosensor according to claim 11 wherein said first structural layer abuts a bottom surface of said bioactive region; and wherein said second structural layer laterally surrounds said bioactive region.

14. The biosensor according to claim 11 wherein said bioactive region, said first structural layer, and said second structural layer each comprises at least one of a monomer and a pre-polymer.

15. A method for manufacturing a biosensor for sensing analytes in a fluid, the method comprising:
   forming a first structural layer comprising a first hydrogel on a substrate;
   forming a second structural layer comprising a second hydrogel;
   forming a bioactive region extending between the first structural layer and the second structural layer and comprising a third hydrogel;
   forming a first electrode coupled to the bioactive region;
   forming a second electrode coupled to the first structural layer and being spaced apart from the first electrode and the bioactive region, wherein a bottom surface of the second electrode is coplanar with a bottom surface of the first electrode in a first electrode portion over a surface of the substrate and in a second electrode portion over a surface of the first structural layer, and wherein the bottom surface of the first electrode and the bottom surface of the second electrode are immediately adjacent to a sidewall of the first structural layer in a third electrode portion between the first electrode portion and the second electrode portion; and
   forming a through opening in the second structural layer adjacent the bioactive region so that the bioactive region is in fluid communication with an environment external to the biosensor for receiving the fluid comprising the analytes.

16. The method according to claim 15 wherein the bioactive region is coupled to the first structural layer and with the second structural layer.

17. The method according to claim 15 wherein the first structural layer abuts a bottom surface of the bioactive region; and wherein the second structural layer laterally surrounds the bioactive region.

18. The method according to claim 15 wherein the bioactive region, the first structural layer, and the second structural layer each comprises at least one of a monomer, an oligomer, and a pre-polymer.

19. The method according to claim 15 further comprising forming a third electrode coupled to the first structural layer and spaced apart from the bioactive region.

20. The method according to claim 19 further comprising coupling a potentiostat to the first electrode, the second electrode, and the third electrode and configured to keep the first electrode at a constant potential with respect to the third electrode so that an electric current circulates between the first electrode and the second electrode; and wherein the electric current indicates a concentration of electroactive species present in the analytes.

* * * * *